United States Patent
Asogawa et al.

(10) Patent No.: US 8,470,266 B2
(45) Date of Patent: Jun. 25, 2013

(54) SAMPLE PACKING DEVICE

(75) Inventors: Minoru Asogawa, Tokyo (JP); Hisashi Hagiwara, Kanagawa (JP); Tohru Hiramatsu, Nagano (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 12/677,471

(22) PCT Filed: Sep. 5, 2008

(86) PCT No.: PCT/JP2008/066478
§ 371 (c)(1),
(2), (4) Date: Mar. 10, 2010

(87) PCT Pub. No.: WO2009/035062
PCT Pub. Date: Mar. 19, 2009

(65) Prior Publication Data
US 2011/0002812 A1    Jan. 6, 2011

(30) Foreign Application Priority Data
Sep. 10, 2007   (JP) .................................. 2007-234163

(51) Int. Cl.
*G01N 31/00* (2006.01)

(52) U.S. Cl.
USPC .......... 422/547; 422/68.1; 422/129; 422/243; 422/502; 422/503; 422/504; 422/512; 422/521; 422/550; 422/560; 435/287.1; 435/287.6; 206/532; 206/730; 220/502

(58) Field of Classification Search
USPC ................ 422/68.1, 129, 500–507, 512, 522, 422/537, 538, 544, 547, 555, 560, 561, 600, 603, 550; 435/287.1–287.3, 287.6
See application file for complete search history.

(56) References Cited

U.S. PATENT DOCUMENTS

| 5,853,101 | A | * | 12/1998 | Weinstein ................ 220/284 |
| 7,473,397 | B2 | | 1/2009 | Griffin et al. |
| 7,476,360 | B2 | | 1/2009 | Gau et al. |
| 2004/0241042 | A1 | * | 12/2004 | Pugia et al. ................ 422/58 |
| 2005/0196855 | A1 | | 9/2005 | Gau et al. |
| 2005/0272169 | A1 | | 12/2005 | Griffin et al. |

(Continued)

FOREIGN PATENT DOCUMENTS

| GB | 1 331503 | 9/1973 |
| JP | 2005-512071 | 4/2005 |

(Continued)

OTHER PUBLICATIONS

International Search Report, PCT/JP2008/066478, Dec. 2, 2008.

(Continued)

*Primary Examiner* — Jill Warden
*Assistant Examiner* — Timothy G Kingan
(74) *Attorney, Agent, or Firm* — Young & Thompson (57) ABSTRACT

Provided is a sample packing device for packing a sample with respect to a microchip for performing reaction of a micro component contained in the sample, the microchip at least including: a sample reservoir; a reaction reservoir; and a channel connected between the sample reservoir and the reaction reservoir, in which a package including a sample chamber packed in advance with the sample is mounted on the microchip so as to pack the sample in the sample chamber into the sample reservoir.

16 Claims, 5 Drawing Sheets

U.S. PATENT DOCUMENTS

| | | | |
|---|---|---|---|
| 2006/0245972 A1 | 11/2006 | Osone et al. | |
| 2006/0275852 A1* | 12/2006 | Montagu et al. | 435/7.93 |
| 2007/0077170 A1 | 4/2007 | Tanaami et al. | |
| 2007/0098770 A1* | 5/2007 | Shikinami et al. | 424/449 |
| 2007/0290065 A1* | 12/2007 | Brown et al. | 239/44 |

FOREIGN PATENT DOCUMENTS

| | | |
|---|---|---|
| JP | 2005-313908 | 11/2005 |
| JP | 2006-308366 | 11/2006 |
| JP | 2006-0329764 | 12/2006 |
| JP | 2007-500850 | 1/2007 |
| JP | 2007-101200 | 4/2007 |
| JP | 2007-522441 | 8/2007 |

OTHER PUBLICATIONS

Official Action dated Feb. 6, 2013 issued by the Japanese Patent Office in corresponding Japanese Patent Application No. 2009-532230 with English translation of relevant part, 5 pages.

* cited by examiner

SAMPLE PACKING DEVICE

TECHNICAL FIELD

This invention relates to a sample packing device for injecting a sample into a microchip including a plurality of reaction reservoirs and sample reservoirs which are used for gene analysis or the like, and, in addition, which are connected to each other through a micro channel.

BACKGROUND ART

In recent years, as described in "Biochemical/Micro Chemical Analysis Systems" (Non-patent Document 1) written by Shuichi Shoji at Waseda University, and Japanese Unexamined Patent Application Publication (JP-A) No. 2007-101200 (Patent Document 2), in a microchip, a lab-on-a-chip, a micro reactor, a micro-fluidic chip, and a chip called a cartridge for chemical reaction in which a packing container and a micro channel are provided on one chip, various liquid-delivering mechanisms and methods for delivering and reacting a sample and a liquid sample so as to analyze a gene has been studied.

According to Non-patent Document 1 described above, "a conceptual view of a system integrated on one substrate includes a pump, which controls a sample-introducing mechanism, a carrier solution, and a flow of the sample, a mix/reaction equipment with a reagent, a component-separating portion, and a sensor portion. There is proposed a microchip as a hybrid-type system, which micronizes each component, forms the channel therein, arranges each component on a substrate, and connects each component through an O-ring or the like". In addition, introduction of the sample required for analysis on the microchip is performed through an exterior micro pump.

Further, according to Patent Document 2 described above, as "a sample-containing portion receiving the sample from outside in a chemical reaction cartridge, which delivers or seals a content for performing chemical reaction by deformation when exterior force is applied", a chemical reaction cartridge has been proposed. In addition, in Patent Document 2 described above, there are described that, at a step of injecting the sample at an initial stage, "the sample is injected through an injection needle or the like".

DISCLOSURE OF THE INVENTION

Problems to be Solved by the Invention

However, the conventional technology in liquid delivery described in Patent Document 1 described above includes a means for injecting the sample from outside of the microchip through the micro pump or the like into a sample reservoir in the microchip. As a result, a liquid-delivering means, which is highly-accurately controlled outside of microchip, is needed. Further, when an analysis step is changed, the entire of the liquid-delivering means is needed to be cleaned and interchanged. In addition, analysis of a micro sample needs a micro-amount-liquid-delivering device of high accuracy, and hence there is a problem in that high cost and a large installing space is needed.

Further, the chemical reaction cartridge described in Patent Document 2 described above uses a means such as the injection needle as a means for initially injecting a specimen and the sample. As a result, miss caused by man of sample selection, sample injection and reagent amount, air mix, or the like may be occurred, and mutual contamination due to dipping reagent may be occurred.

Further, for a sample bottle or the like requiring refrigerant storage, it is necessary to take out the sample bottle or the like from a storage at each time, collect a necessary amount, and put back into the storage, which adversely influences the sample due to temperature change.

Therefore, the preset invention has been made in view of the problems in the above-mentioned conventional technology, and an object of this invention is to provide a sample packing device capable of eliminating occurrence of false injection by a worker, false in injecting amount, and contamination of a sample, further capable of taking out and injecting the sample by a required amount at an appropriate time from a storing place, and including an easy mechanism, which is compactified and inexpensive.

Means to Solve the Problem

In order to achieve the above-mentioned object, in a sample packing device for packing a sample with respect to a microchip for performing reaction of a micro component contained in the sample, the microchip at least includes: a sample reservoir; a reaction reservoir; and a channel connected between the sample reservoir and the reaction reservoir, in which a package includes a sample chamber packed in advance with the sample is mounted on the microchip so as to pack the sample in the sample chamber into the sample reservoir.

Effect of the Invention

According to this invention, false manipulation of the kind and the amount of samples by a worker can be prevented, and the work thereof is simplified, the load of the worker is reduced, and productivity can be increased. In addition, the sample amount is saved, the management state is enhanced, and the analysis accuracy is enhanced due to high accuracy of the delivering amount.

BEST MODE FOR EMBODYING THE INVENTION

In the following, embodiments in this invention are described in detail with reference to the drawings.

Figure 1:
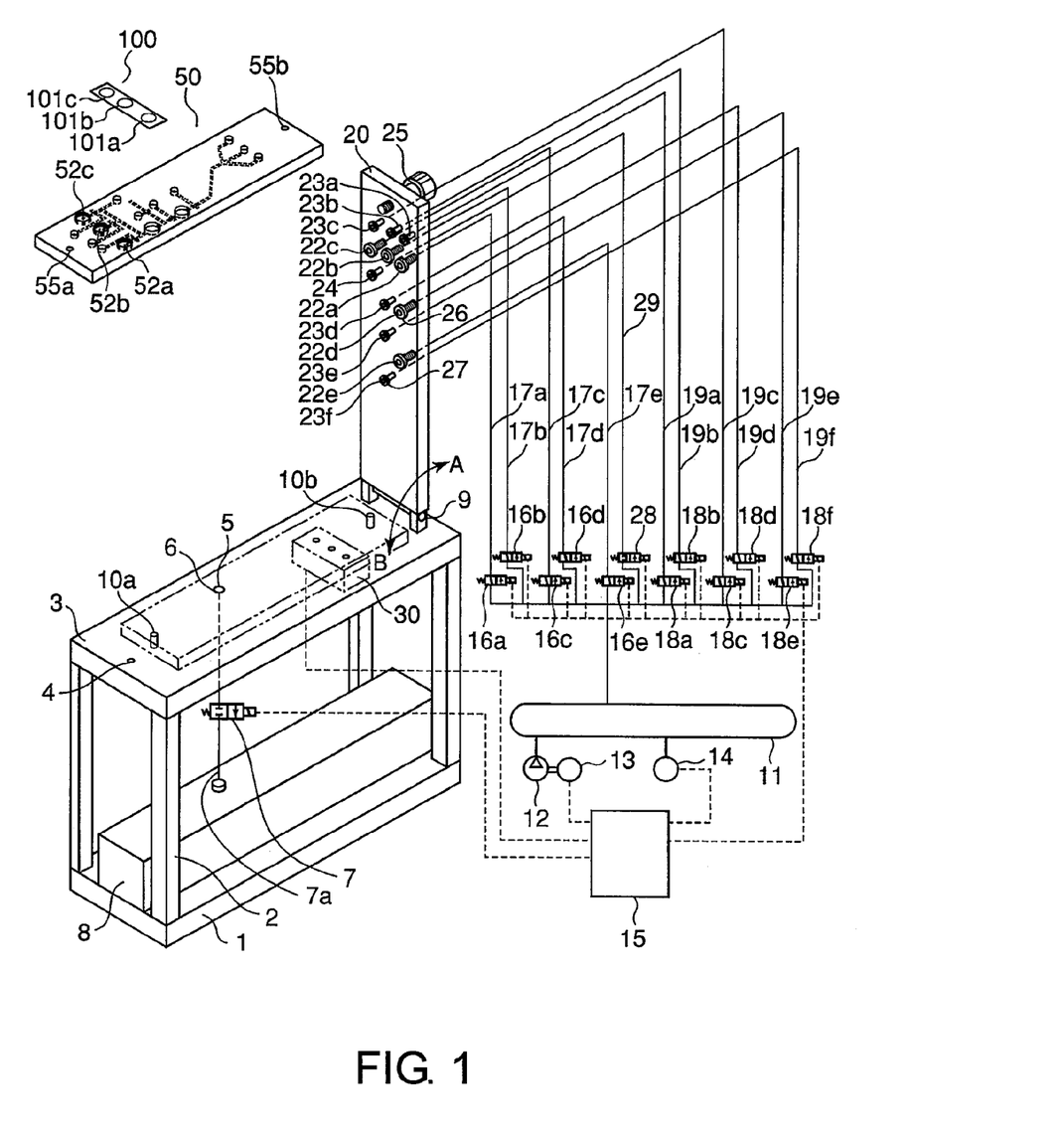
FIG. 1 is a cross-sectional perspective view illustrating a structure of a sample-delivering mechanism of a microchip in an embodiment of this invention.

FIG. 1 is a perspective view illustrating a structure of a device which uses a sample packing device (reagent-introducing mechanism) in this invention, introduces the sample into a microchip, and reacts the sample. Note that pneumatic circuit portions are indicated by logical symbols based on JIS.

On a machine casing 1, a table 3 is provided through poles 2. Further, in a table 3, a disposal hole 5 whose periphery is sealed by an O-ring 6 is provided. The disposal hole 5 is connected to a disposal reservoir 8 provided onto the machine casing 1 through a disposal solenoid-controlled valve 7 and a tube 7a. In an upper surface of the table 3, pins 10a and 10b corresponding to pin holes 55a and 55b provided in a microchip 50 to serves as a guide to a predetermined position are provided in a protruding manner. Further, on the table 3, through a hinge 9, there is provided, so as to be rotatable to the directions A and B, a cover 20 having a fastening screw 25, pressurizing holes 22a, 22b, 22c, 22d, and 22e which pass through the cover 20 and is sealed by an O-ring 26 from the peripheries thereof, shutter pressurizing holes 23a, 23b, 23c, 23d, 23e, and 23f similarly sealed by O-ring 27 from the peripheries thereof, and an air supplying hole 24 similarly sealed by the O-ring 27. Further, in one end on the table 3, a screw hole 4 is provided at a position corresponding to the fastening screw 25.

The pressurizing holes 22a, 22b, 22c, 22d, and 22e which are provided while passing through the cover 20 are electrically connected to secondary sides of pressurizing solenoid-controlled valves 16a, 16b, 16c, 16d, and 16e through tubes 17a, 17b, 17c, 17d, and 17e. Further, shutter pressurizing holes 23a, 23b, 23c, 23d, 23e, and 23f are connected to secondary sides of shutter solenoid-controlled valves 18a, 18b, 18c, 18d, 18e, and 18f through tubes 19a, 19b, 19c, 19d, 19e, and 19f. Further, the air supply tube 24 is connected to the secondary side of an air supply solenoid-controlled valve 28 through a tube 29. Primary sides of the pressurizing solenoid-controlled valves 16a, 16b, 16c, 16d, and 16e, the shutter solenoid-controlled valves 18a, 18b, 18c, 18d, 18e, and 18f, and the air supply solenoid-controlled valve 28 are connected to a pressure accumulator 11. Further, to the pressure accumulator 11, a pump 12 driven by a motor 13 and a pressure sensor 14 for detecting inner pressure are connected. On the table 3, there is provided a temperature adjusting unit 30 for controlling a predetermined portion of the microchip 50 from the lower surface thereof to a predetermined temperature.

Meanwhile, to a controller 15 for executing a predetermined program, there are connected, so as to operationally controlled, the pressurizing solenoid-controlled valves 16a, 16b, 16c, 16d, and 16e, the disposal magnetic hole 7, the shutter solenoid-controlled valves 18a, 18b, 18c, 18d, 18e, and 18f, and the air supply solenoid-controlled valve 28. Further, to the controller 15, the motor 13 and the pressure sensor 14 are connected, the motor 13 driving the pump 12 so as to control the pressure in the pressure accumulator 11 to a predetermined pressure, and the pressure sensor 14 detecting the pressure in the pressure accumulator 11 to perform feedback. With the above-mentioned structure, due to instructions from the controller 15, the pressure in the pressure accumulator 11 is constantly kept in a predetermined pressure. Further, in this structure, the temperature adjusting unit 30 is similarly connected to the controller 15, to thereby perform a temperature control programmed in advance.

Further, a sample package 100 is structured so that sample chambers 101a, 101b, and 101c having convex shapes are inserted into sample reservoirs 52a, 52b, and 52c on a microchip 50. In addition, the microchip 50 is structured so that pin holes 55a and 55b are guided into pins 10a and 10b and is installed on a table 3 so as to be sandwiched by a cover 20 with a fastening screw 25.

Figure 2:
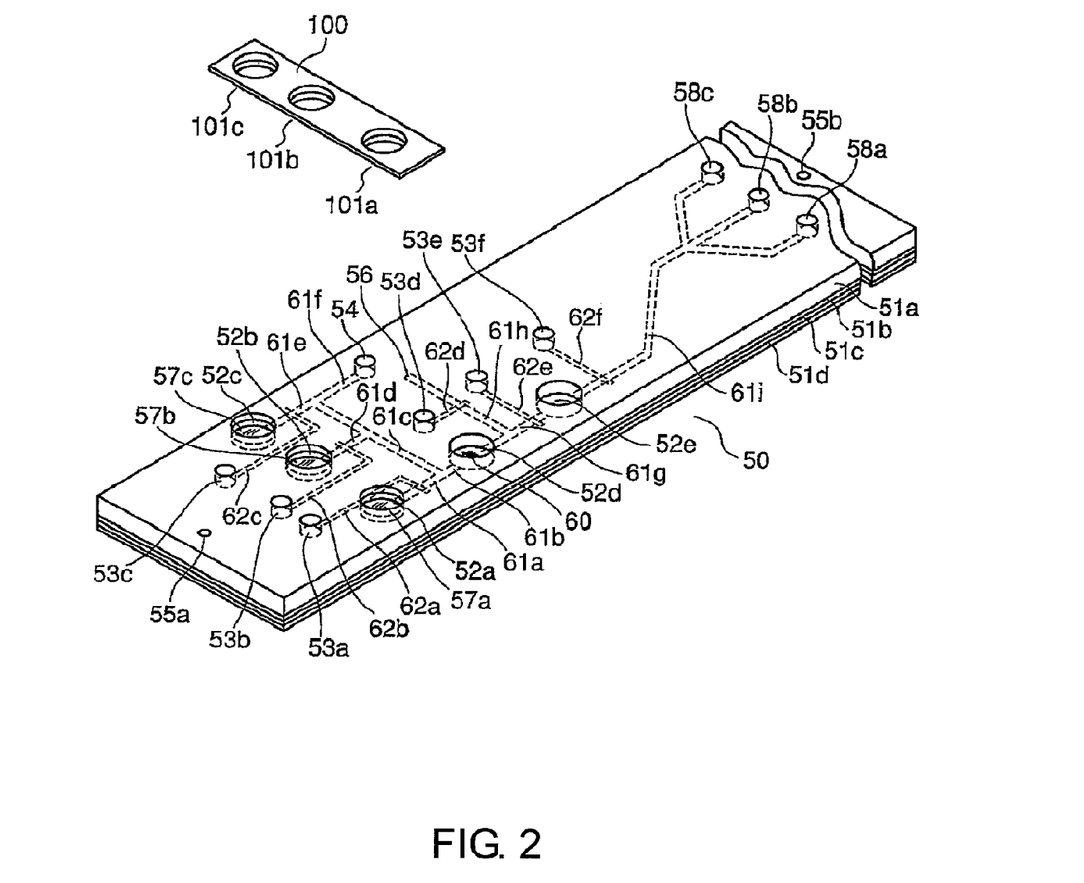
FIG. 2 is a perspective view illustrating a structure of a mechanism of the microchip and a sample package in the embodiment of this invention.

FIG. 2 is a perspective view illustrating details of the sample reservoir package 100 and the microchip 50, which illustrates an embodiment of this invention.

The microchip 50 has a multi-layer structure, in which a main plate 51a, a second plate 51b, a third plate 51c, and a fourth plate 51d, each being made of a flexible resin, are laminated together.

On the microchip, there are provided sample reservoirs 52a, 52b, and 52c, which pass through the main plate 51a and the second plate 51b to be formed into recessed shapes, and an air supply port 54. Further, there are provided a reaction reservoir 52d, an extraction reservoir 52e, and a PCR amplification reservoirs 58a, 58b, and 58c each passing through the main plate 51a to be formed into recessed shapes. Further, on the microchip 50, there are provided shutter ports 53a, 53b, 53c, 53d, 53e, and 53f passing through the main plate 51a, the second plate 51b, and the third plate 51c to be formed into recessed shapes. Further, a disposal hole 56 is provided so as to pass through the second plate 51b, the third plate 51c, and the fourth plate 51d to a lower direction.

Further, when the microchip 50 is installed on the table 3 illustrated in FIG. 1, and the cover 20 is rotated to a B direction, to thereby sandwich the microchip 50 between the table 3 and the cover 20 by the fastening screw 25 and the screw hole 4, the sample reservoirs 52a, 52b, and 52c, the reaction reservoir 52d, the extraction reservoir 52e, and the shutter ports 53a, 53b, 53c, 53d, 53e, and 53f are installed at positions corresponding to the pressurizing holes 22a, 22b, and 22c, the pressurizing hole 22d, the pressurizing hole 22e, and the shutter pressurizing holes 23a, 23b, 23c, 23d, 23e, and 23f, respectively.

Further, the sample reservoirs 52a, 52b, and 53c, the reaction reservoir 52d, the extraction reservoirs 52e, PCR amplification reservoirs 58a, 58b, and 58c, and the air supply port 54 are continuous with each other through channels 61a, 61b, 61c, 61d, 61e, 61f, 61g, 61h, and 61i formed between the main plate 51a and the second plate 51b. Further, shutter ports 53a, 53b, 53c, 53d, 53e, and 53f are continuous with shutter channels 62a, 62b, 62c, 62d, 62e, and 62f, respectively, which are formed between the second plate 51b and the third plate 52c. Further, leading ends thereof are provided so as to intersect the channels 61a, 61b, 61c, 61d, 61e, 61f, 61g, 61h, and 61i through the third plate 51c.

Further, the channels 61a, 61b, 61c, 61d, 61e, 61f, 61g, 61h, and 61i are formed by, when the second plate 51b and the third plate 51c to be formed are bonded to each other, not bonding portions for the channels and by keeping a separable state thereof. Similarly, the shutter channels 62a, 62b, 62c, 62d, 62e, and 62f are formed by, when the third plate 51c and the fourth plate 51d to be formed are bonded to each other, not bonding portions for the channels and by keeping the separable state thereof.

Further, the second plate 51b and the third plate 51c inside the recessed vessel of the reaction reservoir 52d and the extraction reservoirs 52e are also not bonded to each other, to thereby be continuous with the channels 61a, 61b, 61c, 61d, 61e, 61f, 61g, 61h, and 61i. Further, in an unbonded portion formed between the second plate 51b and the third plate 51c inside the reaction reservoir 52d, an adsorption member 60 for extracting a desired micro component is solid-phased.

With the above-mentioned structure, a controller 15 cause, in accordance with a preset program, compressed air in a pressure accumulator 11 to be supplied to pressurizing holes 22a, 22b, and 22c and shutter-pressurizing holes 23a, 23b, 23c, 23d, 23e, and 23f of the cover 20 sequentially through pressurizing solenoid-controlled valves 16a, 16b, 16c, 16d, and 16e, a disposal solenoid-controlled valve 7, shutter solenoid-controlled valves 18a, 18b, 18c, 18d, 18e, and 18f, and an air supply solenoid-controlled valve 28. Further, the compressed air is applied to the sample reservoirs 52a, 52b, and 53c, a reaction reservoir 52d, an extraction reservoir 52e, PCR amplification reservoirs 58a, 58b, and 58c, and an air supply port 54 of the microchip 50.

As a result, there is provided a mechanism in which the compressed air is supplied to the upper side of the sample chambers 101a, 101b, and 101c having convex shapes of the sample package 100 inserted into the sample reservoirs 52a, 52b, and 52c of the microchip 50 so that the sample therein is delivered to the channels 61a, 61d, and 61c of the microchip 50. Note that, the detailed control operation is not directly related to a section of this invention, and hence the description thereof is omitted.

Figure 3A:
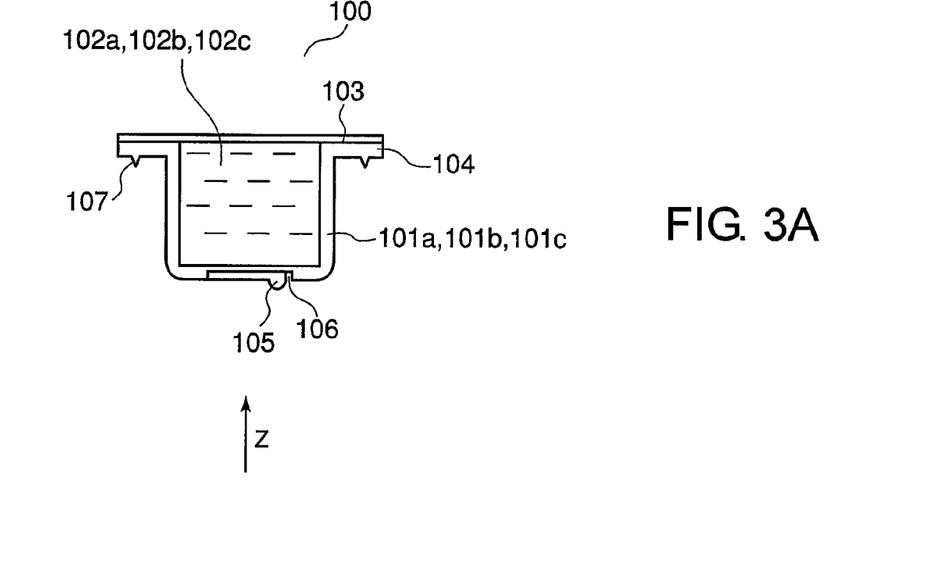
FIG. 3A is a cross-sectional view illustrating the structure of the mechanism of the sample package in the embodiment of this invention.
Figure 3B:
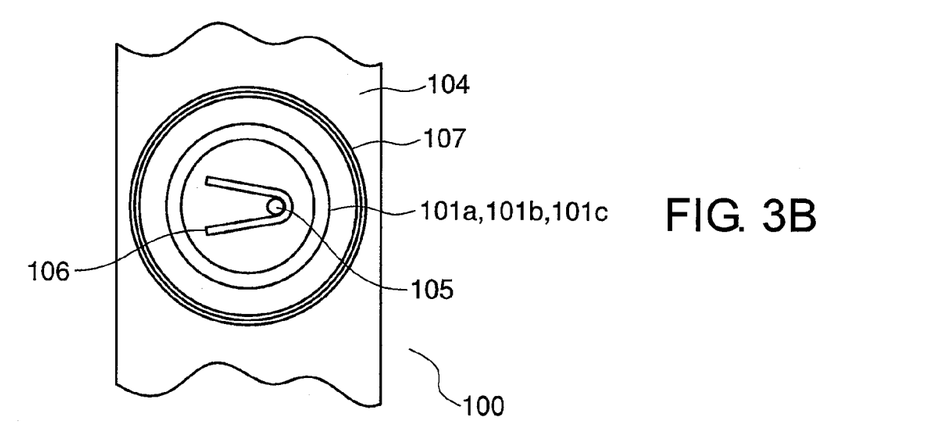
FIG. 3B is a plan view illustrating the structure of the mechanism of the sample package in the embodiment of this invention.

FIG. 3A illustrates a cross-sectional view of the sample package 100. FIG. 3B illustrates a view from the Z direction of FIG. 3A.

First, a structure of the sample package 100 is described with reference to FIG. 3A.

The sample package 100 is provided with the sample chambers 101a, 101b, and 101c having the recessed shapes in the body plate 104. The sample chambers 101a, 101b, and 101c are packed with samples 102a, 102b, and 102c and sealed with a film 103 formed of an elastic body. In a bottom portion of each of the sample chambers 101a, 101b, and 101c, there is provided a portion to be broken 106 having a thin part and a protrusion portion 105. Around each of the sample chambers 101a, 101b, and 101c of the body plate 104, there is provided a seal portion 107 having a keen-cutter-shape.

Next, the structure of the sample package 100 is described with reference to FIG. 3B. Here, FIG. 3B illustrates a part of the sample package 100.

The seal portions 107, which are provided to the body plate 104 of the sample package 100, are provided so as to surround the respective sample chambers 101a, 101b, and 101c. In addition, each of the portions to be broken 106 is provided so as to have a U-shape around the vicinity of the protrusion portion 105. Further, by applying a physical force to the protrusion portion 105 from the outside, the portions to be broken 106 are broken in such way that the portions to be broken 106 are forced into the sample chambers 101a, 101b, and 101c, and the samples 102a, 102b, and 102c, which are packed in the sample chambers 101a, 101b, and 101c illustrated in FIG. 3A, are released to the outside.

Figure 4A:
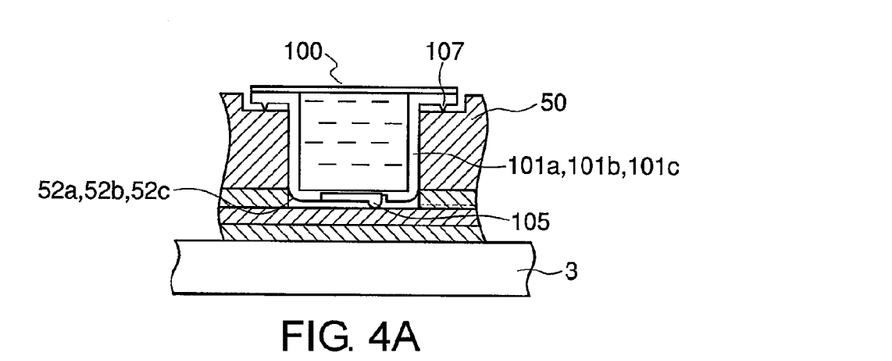
FIG. 4A is a cross-sectional view illustrating an operation of the sample package in the embodiment of this invention.

Next, action upon sample introduction is described with reference to FIG. 4A to FIG. 4C. FIG. 4A illustrates a state in which the microchip 50 is installed on the table 3, and, in addition, the sample chambers 101a, 101b, and 101c of the sample package 100 are inserted into the sample reservoirs 52a, 52b, and 52c on the microchip 50. In this case, the seal portion 107 and the protrusion portion 105 of the sample package 100 are held in contact with one end of the microchip 50.

Next, operation upon sample introduction is described with reference to FIG. 4B.

When the sample package 100 is closed with the cover 20 from the state of FIG. 4A, the sample package 100 is pressed to the C direction due to an O-ring 26 provided to the cover 20. Further, the protrusion portion 105 of the sample package 100 and the sample reservoirs 52a, 52b, and 52c of the microchip 50 are both pressed to the C direction. As a result, the sample chambers 101a, 101b, and 101c are further inserted into the sample reservoirs 52a, 52b, and 52c, and the respective protrusion portions 105 breaks the respective portion to be broken 106. As a result, through the portions to be broken 106, the samples 102a, 102b, and 102c are released to the sample reservoirs 52a, 52b, and 52c.

Further, the seal portion 107 is also pressed against a main plate 51a formed of an elastic member constituting the microchip 50. The seal portions 107 having cutter shapes bite in the main plate 51a, and seal micro gaps 108, which are formed by the sample reservoirs 52a, 52b, and 52c and the sample chambers 101a, 101b, and 101c, from the outside. Parts of the samples 102a, 102b, and 102c released into the sample reservoirs 52a, 52b, and 52c are caused to flow into the gap 108 due to capillarity. With this, when the sample chambers 101a, 101b, and 101c are inserted into the sample reservoirs 52a, 52b, and 52c on the microchip 50, a space medium typified by air mixed into the vicinities of the portions to be broken 106 are pushed up. As a result, the vicinities of the portions to be broken 106 are packed with the samples 102a, 102b, and 102c.

In addition, subsequent operation is described with reference to FIG. 4C.

Figure 4B:
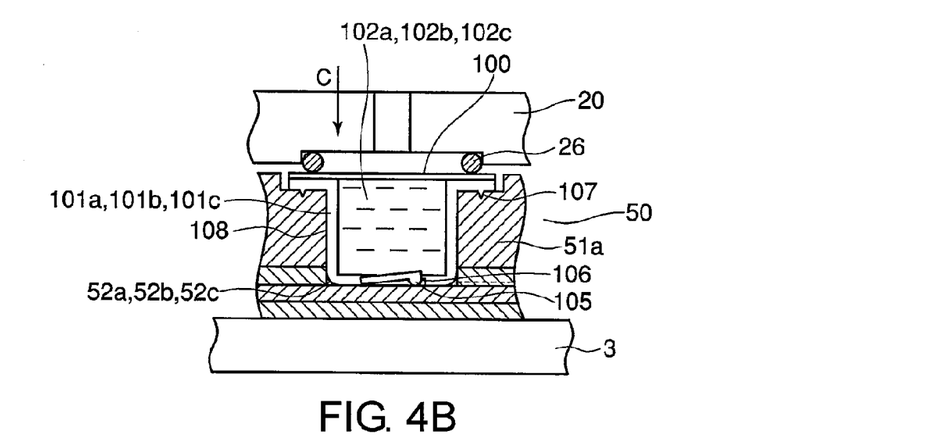
FIG. 4B is a cross-sectional view illustrating the operation of the sample package in the embodiment of this invention.
Figure 4C:
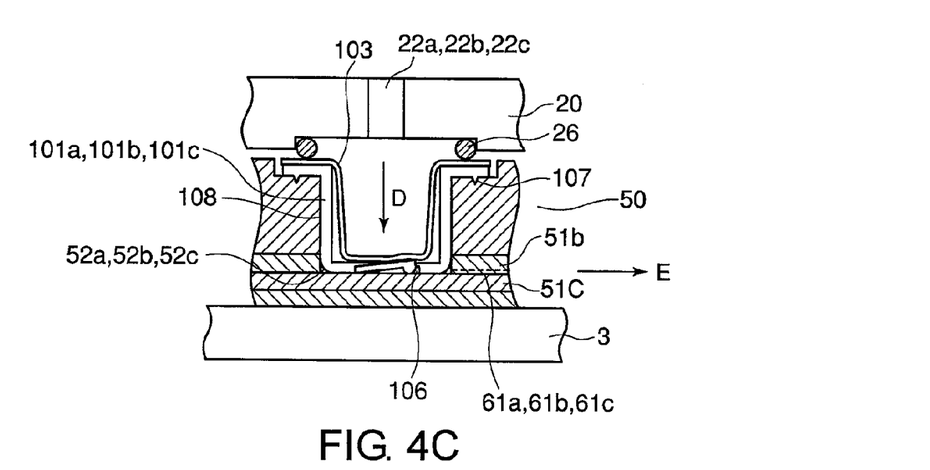
FIG. 4C is a cross-sectional view illustrating the operation of the sample package in the embodiment of this invention.

In FIG. 4C, from the state of FIG. 4B, the compressed air is applied through the pressurizing holes 22a, 22b, and 22c, which are provided to the cover 20, to the D direction by the device and a control means, which are described in FIG. 1. As a result, the films 103 formed of the elastic body are deflected so that the samples 102a, 102b, and 102c are extruded through the portion to be broken 106 to the outside of the sample chambers 101a, 101b, and 101c.

Further, the channels 61a, 61d, and 61e, which are provided between a second plate 51b and a third plate 51c constituting the microchip 50 so that parts of the channels 61a, 61d, and 61e not partially bonded, are opened by the device and the control means described in FIG. 1. In addition, the micro gaps 108 formed of the sample reservoirs 52a, 52b, and 52c and the sample chambers 101a, 101b, and 101c are sealed with the seal portions 107 on the upper side. That is, the samples 102a, 102b, and 102c are injected to the E direction of the microchip 50 through the exclusively opened channels 61a, 61d, and 61e without causing the space medium typified by air to be mixed therein.

Figure 5:
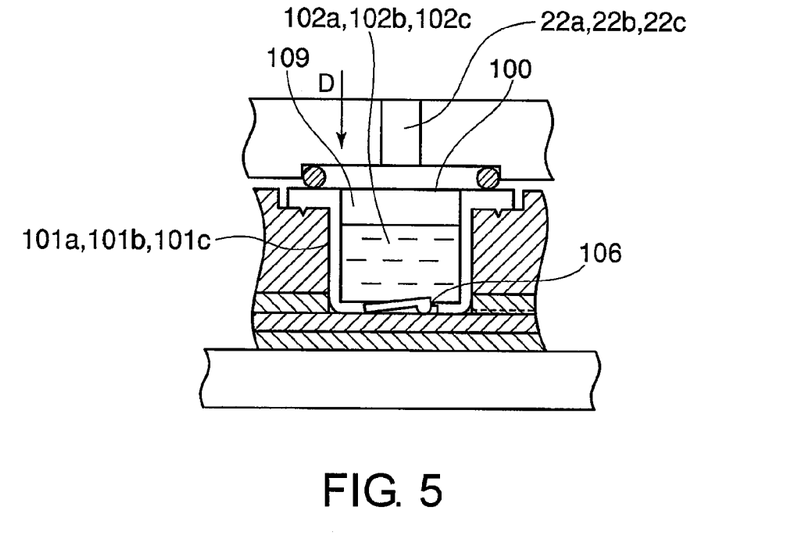
FIG. 5 is a cross-sectional view illustrating a sample package in another embodiment of this invention.

Next, another embodiment is illustrated in FIG. 5.

In FIG. 5, in place of the film 103 illustrated in FIG. 3A, there is provided a movable member 109 having a piston-shape, which seals an inner wall of each of the sample chambers 101a, 101b, and 101c. When the compressed air is applied to the D direction from the pressurizing holes 22a, 22b, and 22c, the movable members 109 extrudes the samples 102a, 102b, and 102c through the portions to be broken 106, and the same effect as that described above is exerted. As described above, in this invention, the kind of means for extruding the samples 102a, 102b, and 102c from the reagent chambers 101a, 101b, and 101c are not limited.

Figure 6:
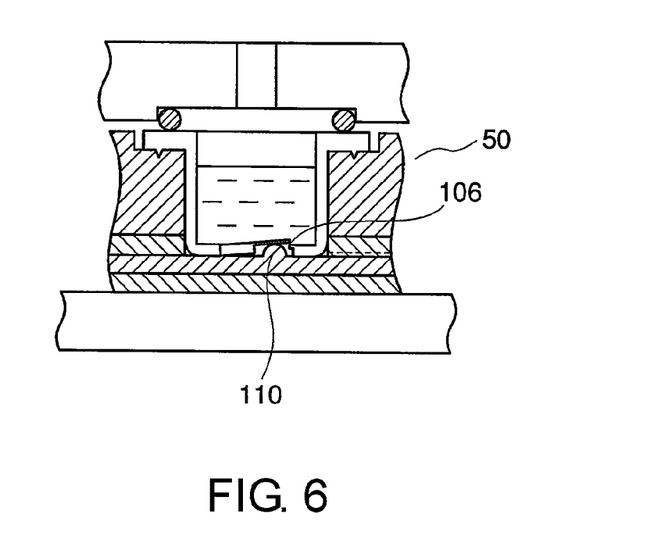
FIG. 6 is a cross-sectional view illustrating a sample package in still another embodiment of this invention.

Next, still another embodiment is illustrated in FIG. 6.

In FIG. 6, in place of the protrusion portion 105 illustrated in FIG. 3A, a contacting surface of the microchip 50 is provided with a convex protrusion portion 110. Also due to the convex protrusion portion 110, the same effect is obtained. As described above, in this invention, the position, at which the convex protrusion portion is provided, is not limited.

Further, though, in the above-mentioned embodiment, the gap portion 108 is described as one having an inserting gap-shape, the same effect is obtained even with a container-shape having a capacity. That is, in this invention, the shape of the gap portion 108 is not limited.

Further, though, the device and the control means of the above-mentioned embodiments are described while using the compressed air, the same effect is obtained even with another pressed medium (for example, liquid, gel, and powder) or the like. As described above, in this invention, the kind of the compressed medium is not limited.

Further, in the above-mentioned embodiment, the portion to be broken 106 is described as one having the U-shape surrounding the vicinity of the protrusion portion 105, the same effect is obtained even with another shape such as a C-shape or a circular shape. As described above, in this invention, the shape of the portion to be broken 106 is not limited.

Further, in the above-mentioned embodiment, though, in FIG. 4A to FIG. 4C, the seal portion 107 having the keen cutter shape is provided to the sample package 100, the same effect is obtained even if the seal portion 107 is provided on the contacting surface of the microchip 50. As described above, in this invention, the position, at which the seal portion 107 is provided, is not limited.

Further, though, in the above-mentioned embodiment, as a means for breaking the portion to be broken 106, the closing action of the cover 20 is used, the same effect is obtained even in insertion with manual operation or another driving means. As described above, in this invention, in this invention, the method of the means for breaking the portion to be broken 106 is not limited.

As described above, in the embodiment of this invention, a container packed with a predetermined amount of sample injected in advance therein is packaged, and hence it is possible to prevent miss by the worker and to efficiently use the sample due to easy work of installing the container to a predetermined position on the microchip. Further, a structure of keeping a storing state of a sample other than the sample currently required is obtained.

Further, the upper surface of the package is sealed with the film formed of the elastic member, and pressed medium is pressed and applied after installation of the device. Thus, a structure of enhancing the accuracy of the injecting amount is obtained.

Further, in the inside of the package, there is provided a movable portion (pressing member) which is capable of moving, and pressed medium is pressed and applied after installation of the device, and hence the movable portion is caused to move. Thus, a structure of enhancing the accuracy of the amount of sample injected into the inside of the package is obtained.

Further, in the bottom portion of the package, there is provided the portion to be broken formed of a weak material or mechanical weak portion, and, on the lower surface of the container forming the package or a receiving portion of the package of the microchip or both of the lower surface of the container forming the package or a receiving portion of the package of the microchip, there is provided a portion having the convex shape so that the package receives locally the physical force when the package is mounted on the microchip in order to promote breaking of the portion to be broken. Thus, a structure of opening the sample by breaking the portion to be broken with a little force is obtained.

Further, the gap portion when the package is mounted on the microchip is structured so as to be micro gap, and hence, upon mounting, the sample leaked due to breaking of a part of the bottom portion causes the medium, which is typified by air entrapped to the gap portion, to be upwardly pushed up due to capillarity. Thus, a structure of preventing the medium from mixing into the channels, to which the sample is injected, of the microchip is obtained.

Further, a seal portion (packing portion) is provided between the package and the microchip so that the seal portion prevents leaking of the pressed medium when the pressed medium is pressed and applied to the package. Thus, a structure of enhancing the accuracy of injecting the sample into the microchip is obtained.

Further, the gap portion when the package is mounted on the microchip is set to be a form having such capacity that the medium, which is typified by air entrapped to the gap portion, is allowed to be accumulated. Thus, a structure of preventing the medium from mixing into the channels of the microchip and promoting the injecting accuracy is obtained.

Further, a plurality of sample chambers are packaged, and hence the work of mounting the plurality of sample chambers to the microchip is significantly simplified. Thus, a structure of promoting the efficiency is obtained.

With the above-mentioned structure, in this embodiment, false manipulation of the kind and the amount of samples by the worker can be prevented, and the work thereof is simplified, the load of the worker is reduced, and productivity can be increased.

In addition, there is no need to take out a sample-stocking bottle and the like from a refrigerant storage, and hence the storing state of the sample is improved.

In addition, recover of extra sample, which is required when the sample is injected with an injector, a pipetter, or the like as in the conventional case, is not required, and hence save of the expensive sample is allowed.

In addition, in such way that the pressed medium is applied to the upper portion of the package, and that the film portion formed of the elastic body is deflected, it is possible to always deliver a sample of a predetermined amount. It is possible to prevent miss or ununiformity by the worker regarding the amount of the sample, and hence the accuracy of the analysis is enhanced.

In addition, the pressed medium is applied to the upper portion of the package, and the movable member (pressing member) which is capable of moving in the package extrudes the sample. Thus, it is possible to always deliver the sample of the predetermined amount. It is possible to prevent miss or ununiformity by the worker regarding the amount of the sample, and hence the accuracy of the analysis is enhanced.

In addition, it is possible that movement of the fixing means operation or the like, which is performed when the package is mounted on the microchip, is transferred to the package so that the portion to be broken is broken and the sample packed therein is released into microchip in an automatic or semi-automatic manner. Thus, the working efficiency can be enhanced and the mutual contamination can be prevented.

In addition, it is possible that air remaining when the package is mounted on the microchip is pushed up along the outer wall of the package due to capillarity when the portion to be broken is broken and the sample packed therein is released, and the air is mixed into the channels of the microchip, which interfere with the analysis, is prevented. Thus, the accuracy of the analysis can be enhanced.

In addition, the seal portion is provided between the package and the microchip so as to prevent the pressed medium from leaking when the pressed medium is applied to the upper portion of the package. Thus, it is possible to efficiently deliver the sample to the microchip.

In addition, there is provided a space portion housing the medium, which is typified by air remaining between the package and the microchip, and hence it becomes easy to push up the air along the outer wall of the package due to capillarity when the portion to be broken is broken and the sample packed therein is released. Thus, the air is mixed into the channels of the microchip, which interfere with the analysis, can be prevented. As a result, the accuracy of the analysis can be enhanced.

In addition, one package is packed with the plurality of samples, and hence it is possible to significantly reduce time period taken for the worker to introduce the sample to the microchip, and to prevent loss of the sample and mutual contamination of the samples.

As described above, in this invention, the sample packing device for packing the sample with respect to the microchip for performing reaction of the micro component contained in the sample, the microchip at least including: a sample reservoir; a reaction reservoir; and a channel connected between the sample reservoir and the reaction reservoir, is characterized in that a package including a sample chamber packed in advance with the sample is mounted on the microchip so as to pack the sample in the sample chamber into the sample reservoir.

Preferably, the sample chamber provided to the package has a convex shape, and the sample chamber is inserted into the sample reservoir provided to the microchip so as to pack the sample in the sample chamber into the sample reservoir.

Preferably, the sample chamber is formed of a film portion including an upper portion formed of an elastic body, and a pressure through a medium is applied from above so as to deflect the film portion so that the sample in the sample chamber is extruded to an outside of the sample chamber.

Preferably, the sample chamber includes a movable portion which is capable of moving when a pressure through the medium is applied from above, and the movable portion is caused to move in the sample chamber so that the sample in the sample chamber is extruded to the outside of the sample chamber.

Preferably, the sample chamber includes a portion to be broken in a bottom portion thereof, the portion to be broken is broken due to a physical force applied from the outside when the package is mounted on the microchip so that the sample in the sample chamber flows into the sample reservoir provided to the microchip.

Preferably, the sample chamber is provided with a protrusion portion in a bottom portion thereof, and the protrusion portion breaks the portion to be broken due to the physical force applied from the outside when the package is mounted on the microchip.

Preferably, the sample reservoir provided to the microchip includes a protrusion portion on an upper surface thereof so as to come into contact with the bottom portion of the sample chamber, and the protrusion portion breaks the portion to be broken due to the physical force applied from the outside when the package is mounted on the microchip.

Preferably, when the package is mounted on the microchip, a gap portion is formed between the sample chamber and the sample reservoir; and when the sample in the sample chamber flows out due to breaking of the portion to be broken, a part of the flown-out sample flows into the gap portion due to capillarity so as to upwardly extrude the medium, which is mixed into a vicinity of the portion to be broken.

Preferably, the sample chamber includes a seal portion around an upper portion thereof so as to seal the gap portion so that the sample is prevented from leaking to the outside when the sample in the sample chamber flows into the sample reservoir.

Preferably, due to the seal portion, the sample in the sample reservoir flows into the channel without causing the medium to be mixed in the sample.

Preferably, the sample flowing into the channel is guided into the reaction reservoir so that a micro component contained in the sample is subject to reaction and analysis.

Preferably, between the sample chamber and the sample reservoir, a space portion having a container shape for accumulating the medium is provided.

Preferably, the package includes a plurality of sample chambers continuously provided thereto. In addition, the microchip includes a plurality of sample reservoirs continuously provided thereto; and an interval between the plurality of sample chambers continuously provided to the package is equal to an interval between the plurality of sample reservoirs continuously provided to the microchip.

In the foregoing, though this invention is specifically described according to the embodiments of this invention, this invention is not limited to the above-mentioned embodiments. It is needless to say that various modifications are possible without departing from the gist of this invention, and those modifications are also enclosed in this application.

This invention is based on Japanese Unexamined Patent Application Publication (JP-A)

No. 2007-234163 A filed on Sep. 10, 2007, and hence contents disclosed in the above-mentioned patent application are all incorporated in this application.

The invention claimed is:

1. A sample packing device for packing a sample with respect to a microchip for performing reaction of a micro component contained in the sample, the microchip at least comprising:
   a sample reservoir;
   a reaction reservoir; and
   a channel connected between the sample reservoir and the reaction reservoir, wherein
   a package comprising a sample chamber packed in advance with the sample is mounted on the microchip so as to pack the sample in the sample chamber into the sample reservoir,
   the sample chamber includes a film portion comprising an upper portion formed of an elastic body,
   the upper portion being bendable by an applied pressure from a medium, and
   the upper portion configured, in response to the upper portion being bent from the applied pressure, to extrude the sample in the sample chamber to an outside of the sample chamber, wherein,
   the sample chamber comprises a portion to be broken in a bottom portion,
   the portion to be broken is broken by a physical force applied from an outside when the package is mounted on the microchip so that the sample in the sample chamber flows into the sample reservoir provided to the microchip,
   the sample chamber is provided with a protrusion portion in a bottom portion, and
   the protrusion portion breaks the portion to be broken by the physical force applied from the outside when the package is mounted on the microchip.

2. A sample packing device according to claim 1, wherein:
   the sample chamber provided to the package has a convex shape; and
   the sample chamber is inserted into the sample reservoir provided to the microchip so as to pack the sample in the sample chamber into the sample reservoir.

3. A sample packing device according to claim 1, wherein:
   the sample reservoir provided to the microchip comprises a protrusion portion on an upper surface so as to come into contact with the bottom portion of the sample chamber; and the protrusion portion breaks the portion to be broken by the physical force applied from the outside when the package is mounted on the microchip.

4. A sample packing device according to claim 1, wherein:
when the package is mounted on the microchip, a gap portion is formed between the sample chamber and the sample reservoir; and
when the sample in the sample chamber flows out by breaking of the portion to be broken, a part of the flown-out sample flows into the gap portion by capillarity so as to upwardly extrude the medium, which is mixed into a vicinity of the portion to be broken.

5. A sample packing device according to claim 4, wherein the sample chamber comprises a seal portion around an upper portion so as to seal the gap portion so that the sample is prevented from leaking to the outside when the sample in the sample chamber flows into the sample reservoir.

6. A sample packing device according to claim 5, wherein, by the seal portion, the sample in the sample reservoir flows into the channel without causing the medium to be mixed in the sample.

7. A sample packing device according to claim 6, wherein the sample flowing into the channel is guided into the reaction reservoir so that a micro component contained in the sample is subject to reaction and analysis.

8. A sample packing device according to claim 1, wherein, between the sample chamber and the sample reservoir, a space portion having a container shape for accumulating the medium is provided.

9. A sample packing device according to claim 1, wherein:
the package comprises a plurality of sample chambers continuously provided thereto;
the microchip comprises a plurality of sample reservoirs continuously provided thereto; and
an interval between the plurality of sample chambers continuously provided to the package is equal to an interval between the plurality of sample reservoirs continuously provided to the microchip.

10. A microchip, wherein the sample packing device according to claim 1 is mounted thereon.

11. A sample processing device for a microchip, wherein the microchip according to claim 10 is installed therein.

12. A sample packing device for packing a sample with respect to a microchip for performing reaction of a micro component contained in the sample, the microchip at least comprising:
a sample reservoir;
a reaction reservoir; and
a channel connected between the sample reservoir and the reaction reservoir, wherein
a package comprising a sample chamber packed in advance with the sample is mounted on the microchip so as to pack the sample in the sample chamber into the sample reservoir, wherein,
the sample chamber comprises a portion to be broken in a bottom portion,
the portion to be broken is broken by a physical force applied from an outside when the package is mounted on the microchip so that the sample in the sample chamber flows into the sample reservoir provided to the microchip,
the sample chamber is provided with a protrusion portion in a bottom portion, and
the protrusion portion breaks the portion to be broken by the physical force applied from the outside when the package is mounted on the microchip.

13. A sample packing device according to claim 12, wherein,
when the package is mounted on the microchip, a gap portion is formed between the sample chamber and the sample reservoir, and
when the sample in the sample chamber flows out by breaking of the portion to be broken, a part of the flown-out sample flows into the gap portion by capillarity so as to upwardly extrude the medium, which is mixed into a vicinity of the portion to be broken.

14. A sample packing device according to claim 12, wherein, between the sample chamber and the sample reservoir, a space portion having a container shape for accumulating the medium is provided.

15. A sample packing device according to claim 12, wherein,
the package comprises a plurality of sample chambers continuously provided thereto;
the microchip comprises a plurality of sample reservoirs continuously provided thereto; and
an interval between the plurality of sample chambers continuously provided to the package is equal to an interval between the plurality of sample reservoirs continuously provided to the microchip.

16. A sample packing device for packing a sample with respect to a microchip for performing reaction of a micro component contained in the sample, the microchip at least comprising:
a sample reservoir (52a);
a reaction reservoir (52d);
a channel connecting the sample reservoir and the reaction reservoir; and
a package (100) comprising a sample chamber (101a) packed in advance with the sample, the package mounted on the microchip so as to pack the sample in the sample chamber into the sample reservoir,
the sample chamber including a film (103) sealed to an upper portion of the sample chamber at a seal portion (107), the film sealing the sample within the sample chamber, the film portion formed of an elastic body, the seal portion (107) resting on an upper surface of the sample reservoir (52a),
the upper portion bendable by an applied pressure from a medium acting on the seal portion (107), and
the upper portion configured, in response to the upper portion being bent downward from the applied pressure, to extrude the sample from inside the sample chamber to outside the sample chamber, wherein,
the sample chamber further comprises a portion to be broken and a protrusion portion in a bottom portion of the sample chamber;
the portion to be broken is configured to be broken by the protrusion portion acting from the applied pressure, breaking the portion to be broken allowing the sample in the sample chamber to flow from inside the sample chamber to the outside the sample chamber and into the sample reservoir.

* * * * *

UNITED STATES PATENT AND TRADEMARK OFFICE
CERTIFICATE OF CORRECTION

PATENT NO. : 8,470,266 B2  Page 1 of 1
APPLICATION NO. : 12/677471
DATED : June 25, 2013
INVENTOR(S) : Asogawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this
Eighth Day of September, 2015

Michelle K. Lee
*Director of the United States Patent and Trademark Office*